(12) United States Patent
Aron et al.

(10) Patent No.: US 6,329,555 B1
(45) Date of Patent: Dec. 11, 2001

(54) PREPARATION OF SUBSTITUTED BUTENES

(75) Inventors: Maik Aron, Freinsheim; Ralf Böhling, Griesheim; Peter Zehner, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/432,202

(22) Filed: Nov. 2, 1999

(30) Foreign Application Priority Data

Nov. 11, 1998 (DE) .............................................. 198 52 006

(51) Int. Cl.⁷ ............................ C07C 41/06; C07C 47/52
(52) U.S. Cl. ...................... 568/689; 568/449; 568/450; 568/487; 568/647; 568/697; 568/904
(58) Field of Search .................. 568/689, 697, 568/647, 487, 449, 450, 904

(56) References Cited

U.S. PATENT DOCUMENTS

| | | | |
|---|---|---|---|
| 2,922,822 | 1/1960 | Beach | 260/614 |
| 4,267,393 | 5/1981 | Torck et al. | 568/697 |
| 4,311,862 | 1/1982 | Drent | 568/689 |
| 5,705,707 | 1/1998 | Kanand et al. | 568/487 |

FOREIGN PATENT DOCUMENTS

| | | | |
|---|---|---|---|
| 25 50 902 | 5/1977 | (DE) | |
| WO 94/00411 | 1/1994 | (WO) | |

*Primary Examiner*—Sreeni Padmanabhan
(74) *Attorney, Agent, or Firm*—Keil & Weinkauf

(57) ABSTRACT

Described is a process for preparing substituted butenes of the formula I and/or II,

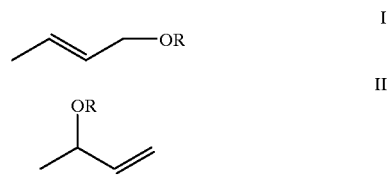

where the radical R is unsubstituted or mono- or di-$C_1$–$C_{10}$-alkoxy-substituted or mono- or dihydroxy-substituted $C_2$–$C_{20}$-alkyl or alkenyl or is $C_6$–$C_{10}$-aryl, $C_7$–$C_{11}$-aralkyl or methyl by reacting 1,3-butadiene with an alcohol of the formula ROH in which R is as defined in the presence of an acidic particulate catalyst insoluble in the reaction medium, which involves contacting the butadiene, the alcohol and the catalyst in a fluidized bed reactor which is flow-approached from below and is operated at above the loosening point.

10 Claims, 3 Drawing Sheets

PREPARATION OF SUBSTITUTED BUTENES

The present invention relates to a process for preparing substituted butenes, especially alkyloxy-, aryloxy- or aralkyloxybutenes.

Substituted butenes of the formula I and/or II

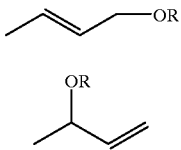

where R is unsubstituted or mono- or di-$C_1$–$C_{10}$-alkoxy-substituted or mono- or dihydroxy-substituted $C_2$–$C_{20}$-alkyl or alkenyl or is $C_6$–$C_{10}$-aryl, $C_7$–$C_{11}$-aralkyl or methyl are important intermediates in the preparation, for example, of n-butyraldehyde and/or n-butanol. They are obtained by reacting 1,3-butadiene with an alcohol. DE 44 00 837 describes a process for preparing n-butyraldehyde and/or n-butanol, wherein the substituted butenes of the formula I and/or II are isomerized to the enol ether of the formula III

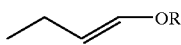

which is reacted with hydrogen and water or water in the presence of a transition metal catalyst to give n-butyraldehyde and/or n-butanol.

For reacting butadiene with the alcohol DE 44 00 837 recommends using solid Bronsted acids, especially organic ion exchangers, which are arranged in a fixed bed traversed in upflow or downflow by the liquid reaction mixture.

It has been found that in the process conceived in DE 44 00 837 there is an increase in the pressure drop along the catalyst bed as the period of operation increases. To manage the increasing pressure drop, therefore, the catalyst has to be replaced at intervals of a few weeks. Examination of the catalyst removed has indicated that the ion exchanger pellets swell in the presence of the reaction medium. Because of this, forces are exerted in the axial and radial directions of the reactor. The ion exchanger pellets in the lower section of the reactor, in particular, are unable to withstand these forces, and undergo deformation. In this way the catalyst bed is compacted and its interstitial volume falls. An increasingly higher pressure must be applied for further throughput of the reaction medium.

The examinations have also shown deposits of a rubber-like polymer covering large areas of the surface of the catalyst particles. Because of these deposits there is a considerable deactivation of the ion exchanger. The deposits are presumed to be polymerization products of the butadiene.

It is an object of the present invention to specify a process which prevents compaction of the catalyst bed and the deposition of polymer on the catalyst surface.

We have found that this object is achieved in accordance with the invention by a process for preparing substituted butenes of the formula I and/or II

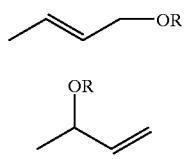

where the radical R is unsubstituted or mono- or di-$C_1$–$C_{10}$-alkoxy-substituted or mono- or dihydroxy-substituted $C_2$–$C_{20}$-alkyl or alkenyl or is $C_6$–$C_{10}$-aryl, $C_7$–$C_{11}$-aralkyl or methyl by reacting 1,3-butadiene with an alcohol of the formula ROH where R is as defined in the presence of an acidic particulate catalyst insoluble in the reaction medium, which comprises contacting the butadiene, the alcohol and the catalyst in a fluidized bed reactor which is flow-approached from below and is operated at above the loosening point.

In the fluidized bed that is flow-approached from below, i.e., against the direction of gravity, the catalyst particles are able to swell without becoming compressed. Frictional contact between the catalyst particles is thought to prevent the formation of polymer deposits.

FIG. 1 shows the relative catalyst activity as a function of the amount of product produced in fixed bed operation and in the fluidized bed operation of the invention.

FIGS. 2 and 3 show scanning electron micrographs of ion exchanger pellets after having been deployed 35 days in fixed bed operation (FIGS. 2a, 2b) or for 20 days in fluidized bed operation (FIGS. 3a, 3b).

1,3-Butadiene is a basic chemical generated in large amounts in steam crackers and isolated by extraction using N-methylpyrrolidone, for example, from the $C_4$ cut of the steam cracker.

In the presence of a catalyst, 1,3-butadiene reacts with the alcohol ROH in accordance with equation (1)

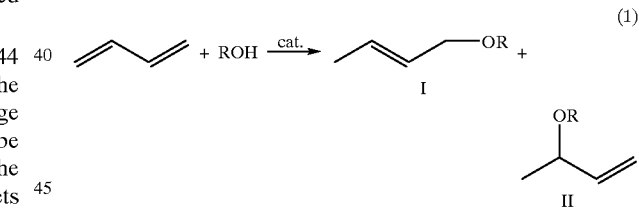

to form the 1,4 adduct of the formula I and the 1,2 adduct of the formula II. Because of the position of the double bond, the 1,4 adduct I exists in both the cis and the trans forms. Depending on the reaction conditions and catalyst employed, the adduct I and II are generally formed in a molar ratio of from 1:1 to 1:3.

The nature of the alcohol ROH employed in the reaction is not generally critical for the process. Both primary and secondary alcohols can be used, although the former are preferred. The alcohols used can be aliphatic, cycloaliphatic, aromatic and araliphatic, preference being given to the use of aliphatic and araliphatic alcohols. In general, in the alcohols ROH used in the process of the invention, the radical R is a $C_1$–$C_{20}$-alkyl or $C_2$–$C_{10}$-alkenyl group, such as the 2-butenyl group, preferably a $C_1$–$C_4$-alkyl group, especially the n-butyl group, a $C_6$–$C_{10}$-aryl group, preferably the phenyl group, or a $C_7$–$C_{11}$-aralkyl group, preferably the benzyl group. The radicals R may if desired carry substituents such as $C_1$–$C_{10}$-alkoxy and/or hydroxyl groups. As a result, diols or triols or alkoxy alcohols may also be used as alcohols ROH. Since the substituents generally have no critical influence on the reaction, it is preferred to use alcohols ROH with unsubstituted radicals R. It is of course also possible to employ alcohols with a higher number of carbon atoms, but since they are generally more expensive than lower alcohols the latter are preferred on economic grounds.

The reaction takes place in the presence of an acidic particulate catalyst which is insoluble in the reaction medium. The use of organic cation exchangers is preferred.

By organic cation exchangers are meant pulverulent, gel-like or macroporous, polymeric polyelectrolytes which carry Brönsted acid functional groups, such as sulfonic, phosphonic or carboxylic acid groups, on a polymeric matrix, examples being sulfonated phenol-formaldehyde resins, sulfonated styrene-divinylbenzene copolymers, sulfonated polystyrene, poly(perfluoroalkylene)-sulfonic acids, and sulfonated carbons. In the process of the invention the cation exchangers are judiciously employed in their protonated form, known as the $H^+$ form. Examples of suitable commercial organic cation exchangers are Amberlite® 200, Amberlite® IR 120, Amberlite® IR 132 E, Lewatit® SC 102, Lewatit® SC 104, Lewatit® SC 108, Lewatit® SPC 108, Lewatit® SPC 112, Lewatit® SPC 118 and Amberlyst® 15, Amberlyst® 35 wet, Amberlyst® 38 wet, Amberlyst® CSP 2, Amberlyst® CSP 3, and Purolite® CT 175.

The acid group content of the ion exchangers is preferably from 4 to 6 and more preferably from 5 to 5.5 eq/kg.

In place of organic acid cation exchangers in the process of the invention it is possible to employ inorganic solids with a Brönsted acid action, examples being zeolites, such as β-zeolites or Y-zeolites in the $H^+$ form, bleaching earths, such as bentonites, montmorillonites and attapulgites, phosphate-based nonzeolite molecular sieves, as claimed, for example, by U.S. Pat. No. 4,440,871, U.S. Pat. No. 4,310,440, U.S. Pat. No. 4,567,029, U.S. Pat. No. 4,554,143, U.S. Pat. No. 4,500,651, EP-A 158 976, EP-A 158 349 and EP-A 159 624, and acidic or acid-impregnated metal oxides, whose preparation is described, for example, in U.S. Pat. No. 4,873,017. Preferred Brönsted acid inorganic solids are β-zeolites or Y-zeolites in the $H^+$ form, especially β-zeolites in the $H^+$ form. β-zeolites are obtainable, for example, by the process of U.S. Pat. No. 4,891,458.

The invention is based on the use of a vertical fluidized bed reactor for contacting the butadiene, the alcohol and the catalyst. The process of the invention is operated with a liquid reaction medium which preferably is essentially homogeneous. The fluid bed state prevails when the linear velocity of a fluid in a bed flow-approached from below is raised above the loosening velocity, so that the individual particles are held in suspension and are homogeneously suspended in the fluid. At the loosening point, the bed is in the state of incipient expansion. The loosening point is determined experimentally by measuring the pressure drop Δp across the fluidized bed as a function of the cross-sectional space velocity. The loosening point is then found to be the intersect between the extrapolated solid-bed line and the constant pressure drop line in the fluidized bed.

The height $l_0$, measured in the vertical direction, of the bed of catalyst in the resting state increases as the reactor is operated, to reach the height L. The difference relative to $l_0$, namely $L-l_0$, is termed the bed expansion. It is preferred for the bed expansion to be at least 5%, more preferably from 7 to 50% and, in particular, from 12 to 15% relative to the resting state.

The volume of reaction medium passed through the bed relative to the reactor cross section (in $m^2$) and the time (in h) is termed the cross-sectional space velocity of the reactor. Under reaction conditions it is preferably from 5 to 100, in particular from 7 to 60 and, with particular preference, from 10 to 30 $m^3/m^2 \cdot h$.

To achieve the reactor cross-sectional space velocity required for fluidized-bed operation it may be judicious to recycle some of the reactor discharge. The return ratio depends heavily on the particular reactor geometry.

For advantageous flow, the catalyst preferably has a defined density (bulk density). The catalyst preferably has a density of from 700 to 900 g/l, in particular from 720 to 850 g/l. Furthermore, the catalyst particles preferably have a defined diameter, which is generally from 0.2 to 1.5 mm, in particular from 0.4 to 1.2 mm.

It has surprisingly been found that it is possible to optimize the novel process further by controlling the pore size distribution of the catalyst. It turned out that the reaction rate is increased, and side reactions suppressed, if the catalyst comprises a porous matrix having a maximum pore radius distribution, determined by the BET method, in the range from 20 to 100 nm, preferably from 40 to 80 nm. The pore radius distribution may exhibit two or more maxima. For present purposes it is sufficient for one maximum (in addition to further maxima which may be present) of the pore radius distribution to lie within the stated range. The pore radius distribution is judiciously determined by the method of Brunauer, Emmett and Teller (BET method). This method involves measuring the volume of nitrogen gas adsorbed by a sample at −196° C. as a function of the pressure applied. The number of pores with the respective diameter is plotted against the diameter. For particulars reference is made to DIN 66131, 1993, Beuth Verlag GmbH, Berlin.

To carry out the measurement, a Micromeritics ASAP 2400 instrument is suitable.

It is believed that the influence of the pore size is based on control over access to the active centers by the reactants. Organic cation exchangers whose polymeric matrix has the specified pore size distribution are particularly preferred.

The molar ratio of alcohol to 1,3-butadiene can be chosen within a broad range in the process of the invention. The feedstream will generally employ a molar ratio of alcohol ROH to 1,3-butadiene of from 0.5:1 to 15:1, preferably from 1:1 to 5:1 and, with particular preference, from 1.8:1 to 3.5:1. Reaction of the alcohol ROH with 1,3-butadiene is generally performed at temperatures from 20 to 130° C., preferably from 50 to 120° C. and, in particular, from 75 to 100° C. and at a pressure of from 3 to 100 bar, preferably from 5 to 50 bar and, in particular, from 7 to 20 bar. It is judicious to choose a pressure such that the 1,3-butadiene is in liquid form at the reaction temperature deployed. Use of a higher pressure is possible.

The addition of a solvent to the reaction mixture is also possible though generally unnecessary since both the alcohol employed and the adducts I and II are also able to act as solvents.

The water content of the reaction mixture is preferably controlled. Too high a water content leads to hydration of the active centers of the catalyst and so hinders access by alcohol and/or 1,3-butadiene. The water concentration is preferably not more than 3% by weight, in particular from 0.1 to 2% by weight.

In a preferred embodiment the alcohol ROH is n-butanol. In this case the mixture exiting the reactor generally has the following composition:

from 1 to 30% by weight, preferably from 3 to 20% by weight and, in particular, from 5 to 15% by weight of 1,3-butadiene, from 4 to 40% by weight, preferably from 6 to 35% by weight and, in particular, from 8 to 30% by weight of 1-butoxybutene, from 4 to 60% by weight, preferably from 8 to 45% by weight and, in particular, from 10 to 35% by weight of 3-butoxybutene, from 20 to 80% by weight, preferably from 30 to 70% by weight and, in particular, from 40 to 65% by weight of n-butanol, and from 0 to 10% by weight, preferably from 0.1 to 3% by weight and, in particular, from 0.2 to 1.2% by weight of water.

The reactor discharge of the process of the invention generally includes not only unreacted 1,3-butadiene but also the adducts of the formulae I and II and, possibly, small amounts of reaction byproducts, such as alkoxyoctadienes, octatriene, vinylcyclohexene, alkoxydodecatrienes, dodecatetraene, dialkoxyoctene and dialkoxybutane. Unreacted butadiene and unreacted alcohol from the reactor discharge are judiciously recycled to the process. If this is done it is generally necessary to remove entrained water which derives from side reactions.

The adduct required to prepare n-butyraldehyde and/or n-butanol is the 1-alkoxy-2-butene of the formula I. Therefore, the adduct II is first of all separated off from the isomeric adduct I present in the reactor discharge.

After separation from the desired adduct, the adduct II can be recycled into the process of the invention. Recycling of the adduct II to the process of the invention causes isomerization of the adduct II to the adduct I in this process stage and leads ultimately to suppression of the formation of new, unwanted adduct II, so that overall virtually none of the isomeric adduct II but instead only the desired adduct I is formed in this circulation process.

In the further course of the process for preparing n-butyraldehyde and/or n-butanol the adduct I is catalytically isomerized to the enol ether of the formula III, which is subsequently catalytically hydrolyzed in the presence of water to form n-butyraldehyde and/or catalytically converted, in the presence of water and hydrogen, to n-butanol (see equation (2)). These component reactions may be carried out either in succession in two stages of the process or in succession in a single reactor or, with particular preference, in a single process stage. Both component reactions may take place either in the gas phase or in liquid phase. Suitable catalysts are transition element catalysts.

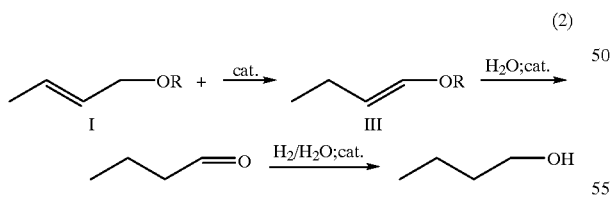

(2)

Regarding the reaction conditions and applicable catalysts for the further reaction of the substituted butenes I and/or II to the enol ether III and on to n-butyraldehyde and/or n-butanol, reference is made to DE 44 00 837. It is preferred to conduct the isomerization and the further reaction in one process stage. Examples of suitable catalysts are unidentate or multidentate phosphine or phosphite complexes of an element from Group Ib, VIb, VIIb and/or VIIIb of the Periodic Table of the Elements. Also suitable are complexes of nitrogenous chelate ligands, such as bipyridine or phenanthroline ligands, with an element from Group Ib, VIb, VIIb and/or VIIIb of the Periodic Table of the Elements. It is also possible to use salts of an element from Group Ib, VIb, VIIb and/or VIIIb of the Periodic Table of the Elements. Also suitable, finally, are aquo, ammine, halo, cyano, carbonyl, amino and/or acetylacetonato complexes of an element from Group Ib, VIb, VIIb and/or VIIIb of the Periodic Table of the Elements.

The invention is illustrated by the examples below.

EXAMPLE 1

The addition reaction of n-butanol to 1,3-butadiene was conducted in the presence of an acidic ion exchanger in fluidized bed operation in a glass reactor. The experimental parameters were as follows:

Temperature: 80° C.

Pressure: 10 bar

Feedstream flow rate: 13 g/h

Feedstream composition: 80% by weight butanol,
  19.9% by weight butadiene,
  0.1% by weight $H_2O$ Reactor diameter: 20 mm Bed height (unexpanded): 135 mm Catalyst: ion exchanger Purolite CT-175

Pellet diameter: 0.3–1.2 mm

Circulation flow: 3.1 kg/h

Liquid space velocity: 12.4 $m^3/m^2 \cdot h$

Bed expansion: 10 mm

The ion exchanger was in the form of pellets with a diameter of 0.3–1.2 mm. Its density was 750–850 g/l, and its acid group content 5 eq/kg. The pore radius distribution had a maximum at 45 mm. No increase in the pressure drop was observed during the experimental period of 600 h. The relative activity based on the initial activity (which was taken as 100) of the catalyst as a function of the amount of 1-butoxy-2-butene produced from the beginning of the experiment is plotted in FIG. 1 (hollow circles and solid squares respectively; the measurements come from two experiments). The feedstream flow rate was varied so as to give steady state reactant concentrations. It had to be reduced as the experiment progressed, on account of the decreasing catalyst activity.

EXAMPLE 2

Example 1 was repeated with the following experimental parameters:

Temperature: 80° C.

Pressure: 10 bar

Feedstream flow rate: 13 g/h

Feedstream composition: 80% by weight butanol,
  19.9% by weight butadiene,
  0.1% by weight $H_2O$ Reactor diameter: 20 mm Bed height (unexpanded): 137 mm Catalyst: ion exchanger Amberlyst CSP 2

Pellet diameter: 0.4–1.2 mm

Circulation flow: 5.6 kg/h

Liquid space velocity: 22.4 $m^3/m^2 \cdot h$

Bed expansion: 20 mm

COMPARATIVE EXAMPLE

The addition reaction of n-butanol to butadiene was conducted with the same feedstream composition and ion exchanger as in Example 1 above but in a fixed bed flow-traversed from above. The experimental parameters were otherwise as specified in Example 1.

BRIEF DESCRIPTION OF THE DRAWINGS

The relative activity of the catalyst (based on the initial activity, which was taken as 100%) as a function of the amount of 1-butoxy-2-butene produced from the beginning of the experiment is depicted in FIG. 1 (solid diamonds). This figure shows that catalyst deactivation in fixed bed operation is much more rapid than in fluidized bed operation.

Further, scanning electron micrographs were taken of an ion exchanger pellet following 35 days' deployment in the fixed bed (FIG. 2a, FIG. 2b) and, respectively, after 20 days in fluidized bed operation (FIG. 3a, FIG. 3b).

Figure 1:
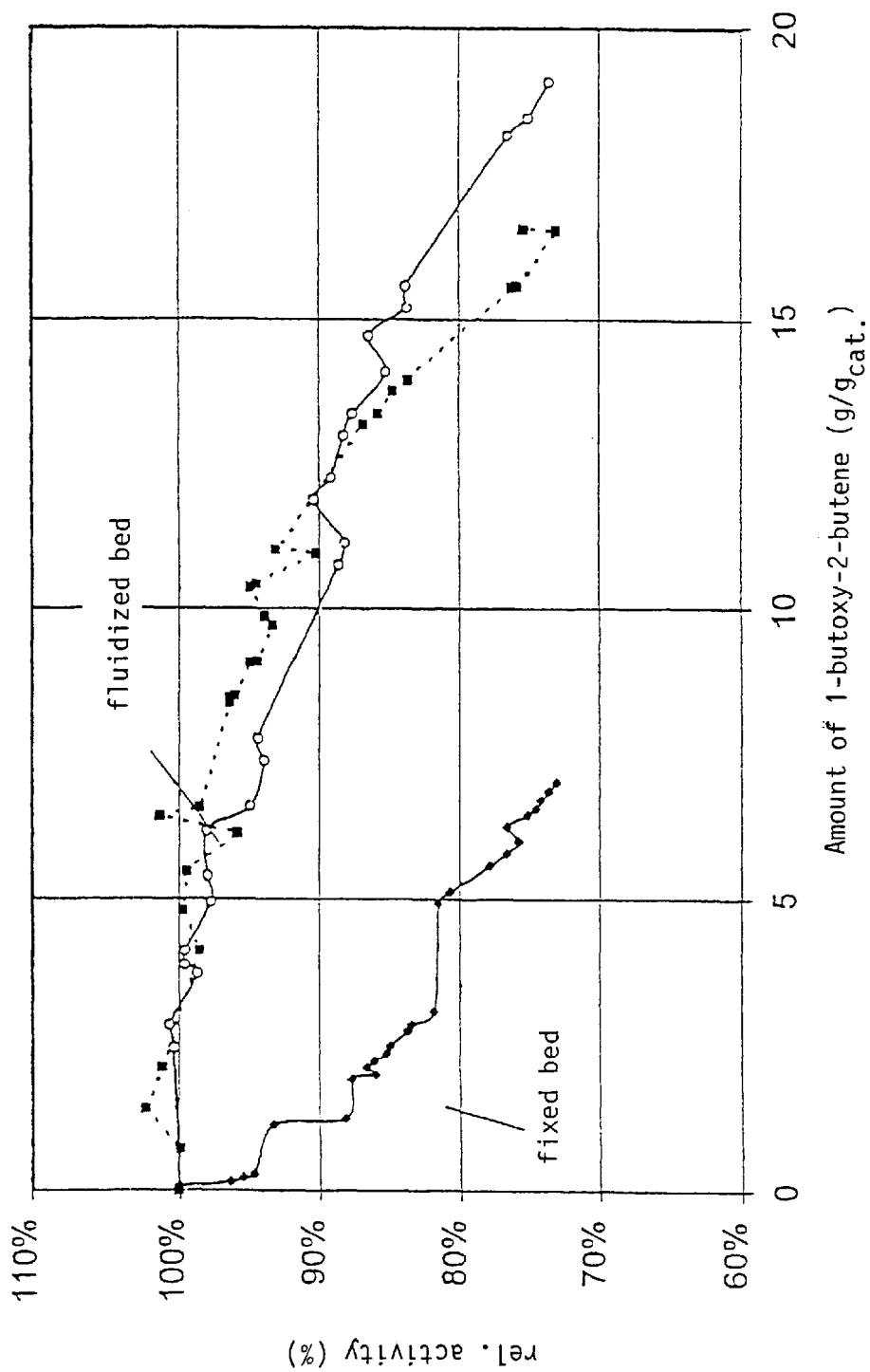
Figure 2A:
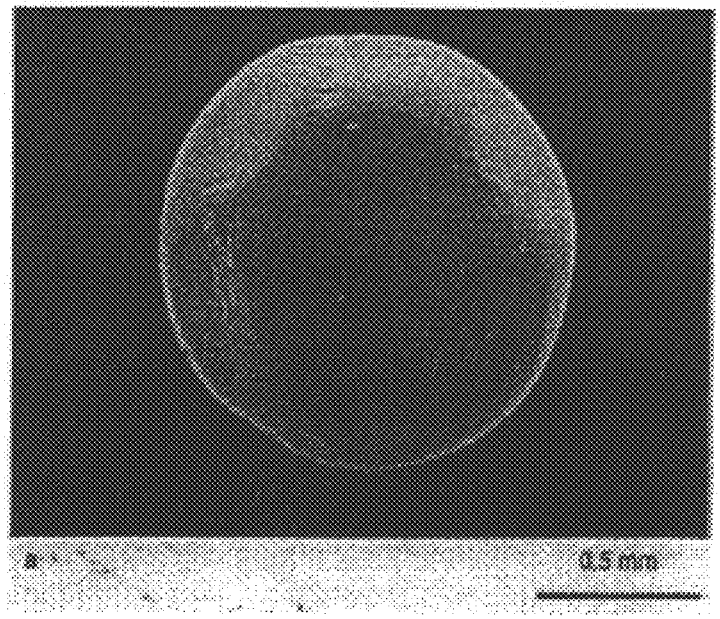
FIG. 2a clearly shows the swelling-induced deformation of the ion exchanger pellets, which results in compression of the fixed bed, while FIG. 2b reveals deposits of rubberlike polymers which cause rapid deactivation of the catalyst.
Figure 2B:
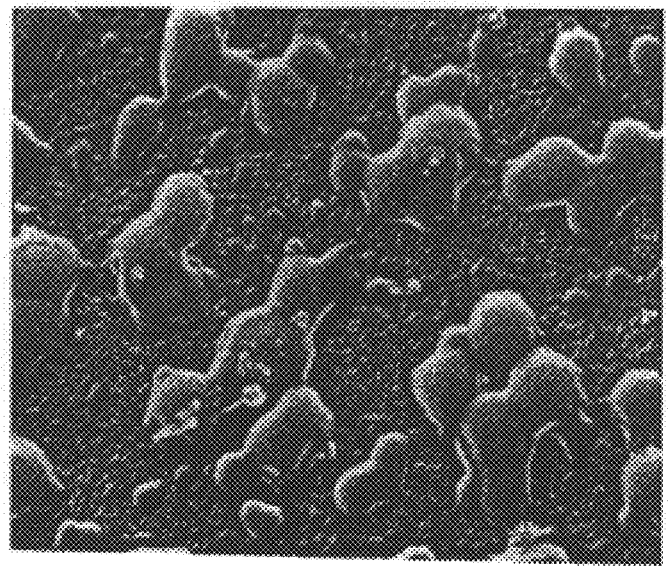
Figure 3A:
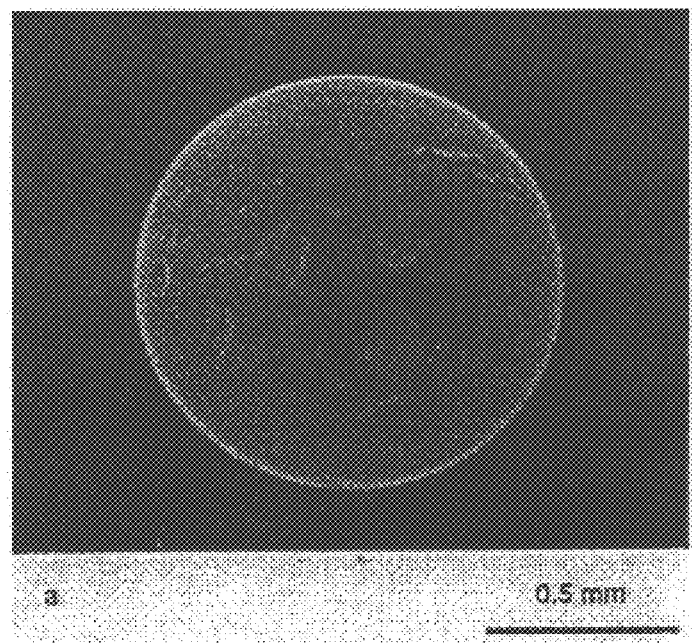
FIG. 3a shows the SEM image of an ion exchanger pellet after 20 days in fluidized bed operation. The pellet shows no traces of deformation whatsoever. The ion exchanger pellet also showed virtually no polymer deposits after 20 days in fluidized bed operation (FIG. 3b).
Figure 3B:
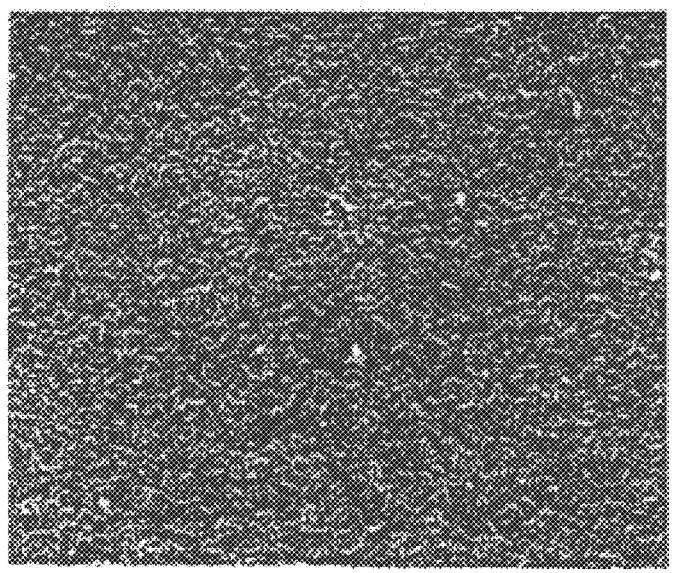

We claim:

1. A process for preparing substituted butenes of the formula I and/or II,

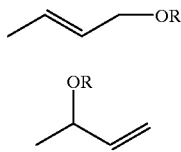

where the radical R is $C_2$–$C_{20}$-alkyl, $C_2$–$C_{20}$-alkenyl, $C_6$–$C_{10}$-aryl, $C_7$–$C_{11}$-aralkyl, or methyl, wherein the alkyl and alkenyl groups may be substituted by one or two substituents selected from $C_1$–$C_{10}$-alkoxy and hydroxy, by reacting 1,3-butadiene with an alcohol of the formula ROH in which R is as defined above, in the presence of an acidic particulate catalyst insoluble in the reaction medium, which comprises introducing a liquid reaction medium, which contains the butadiene and the alcohol, against the direction of gravity from below into a fluidized bed reactor containing the catalyst, at such a linear velocity that the fluidized bed reactor is operated at above the loosening point.

2. A process as claimed in claim 1, wherein the bed expansion during operation of the reactor is at least 5%.

3. A process as claimed in claim 1, wherein the cross-sectional space velocity of the reactor is from 5 to 100 $m^3/m^2 \cdot h$.

4. A process as claimed in claim 1, wherein said catalyst is in the form of particles with a diameter of from 0.2 to 1.5 mm.

5. A process as claimed in claim 1, wherein said catalyst has a density of from 700 to 900 g/l.

6. A process as claimed in claim 1, wherein said catalyst is an organic cation exchanger.

7. A process as claimed in claim 6, wherein said ion exchanger has an acid group content of from 4 to 6 eq/kg.

8. A process as claimed in claim 1, wherein said catalyst comprises a porous matrix having a pore radius distribution, determined by the BET method, the peak of which is in the range from 20 to 100 nm.

9. A process as claimed in claim 1, wherein part of the reactor discharge is recycled.

10. A process as claimed in claim 1, wherein said substituted butene of the formula I is isomerized in the presence of a transition metal catalyst to give the enol ether of the formula III

which is reacted with hydrogen and water or water in the presence of a transition metal catalyst to give n-butyraldehyde and/or n-butanol.

* * * * *